(12) United States Patent
Daniele et al.

(10) Patent No.: US 12,324,654 B2
(45) Date of Patent: Jun. 10, 2025

(54) FETAL HEALTH MONITORING SYSTEM AND METHOD FOR USING THE SAME

(71) Applicant: North Carolina State University, Raleigh, NC (US)

(72) Inventors: Michael Daniele, Raleigh, NC (US); Michael Wilkins, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 415 days.

(21) Appl. No.: 17/336,547

(22) Filed: Jun. 2, 2021

(65) Prior Publication Data
US 2021/0378585 A1 Dec. 9, 2021

Related U.S. Application Data

(60) Provisional application No. 63/034,146, filed on Jun. 3, 2020.

(51) Int. Cl.
*A61B 5/024* (2006.01)
*A61B 5/00* (2006.01)
(Continued)

(52) U.S. Cl.
CPC ........ *A61B 5/02411* (2013.01); *A61B 5/0205* (2013.01); *A61B 5/14551* (2013.01);
(Continued)

(58) Field of Classification Search
CPC . A61B 5/02411; A61B 5/0205; A61B 5/7203; A61B 5/7278; A61B 7/00; A61B 5/02405
See application file for complete search history.

(56) References Cited

U.S. PATENT DOCUMENTS 4,086,917 A 5/1978 Bruks et al.
4,157,710 A 6/1979 Abitbol
(Continued)

FOREIGN PATENT DOCUMENTS

RU 2656518 C2 * 6/2018
WO WO-2014162135 A1 * 10/2014 ........... A61B 5/0011
(Continued)

OTHER PUBLICATIONS

Khandoker, A., Ibrahim, E., Oshio, S. et al. Validation of beat by beat fetal heart signals acquired from four-channel fetal phonocardiogram with fetal electrocardiogram in healthy late pregnancy. Sci Rep 8, 13635 (2018). https://doi.org/10.1038/s41598-018-31898-1 (Year: 2018).*

(Continued)

*Primary Examiner* — Shirley X Jian
*Assistant Examiner* — Laura Hodge
(74) *Attorney, Agent, or Firm* — NK Patent Law

(57) ABSTRACT

Wearable fetal health monitoring device for determining a heath condition of a fetus based on biosignals of an expecting mother and the fetus is provided. The device includes a MEMS accelerometer that converts an acoustic wave sensed in an abdominal region into an abdominal acoustic signal. The device also includes a pulse oximeter generates a maternal photoplethysmogram (mPPG) value from a pulse sensed in the abdominal region. The device further includes a microcontroller configured to: generate a maternal phonocardiogram (mPCG) value from the abdominal acoustic signal; calculate a first maternal heart rate (mHR) value from the mPCG value; calculate a second mHR value from the mPPG value; compare the first mHR value with the second mHR value to identify a noise correction value; and apply the identified noise correction value to the mPCG value to extract a fetal phonocardiogram (fPCG) value.

18 Claims, 10 Drawing Sheets

(51) Int. Cl.
    *A61B 5/0205* (2006.01)
    *A61B 5/11* (2006.01)
    *A61B 5/1455* (2006.01)
    *A61B 7/00* (2006.01)

(52) U.S. Cl.
    CPC .......... *A61B 5/4362* (2013.01); *A61B 5/6823* (2013.01); *A61B 5/6832* (2013.01); *A61B 5/7203* (2013.01); *A61B 5/7278* (2013.01); *A61B 7/00* (2013.01); *A61B 5/02405* (2013.01); *A61B 5/1118* (2013.01)

(56) References Cited

U.S. PATENT DOCUMENTS

| | | | |
|---|---|---|---|
| 5,411,024 A | 5/1995 | Thomas et al. | |
| 5,431,171 A | 7/1995 | Harrison et al. | |
| 5,749,831 A | 5/1998 | Baker | |
| 6,122,536 A | 9/2000 | Sun et al. | |
| 6,267,724 B1 | 7/2001 | Taylor | |
| 6,673,596 B1 | 1/2004 | Sayler et al. | |
| 6,749,574 B2 | 7/2004 | O'Keefe | |
| 6,912,424 B2 | 6/2005 | Bishay et al. | |
| 6,965,791 B1 | 11/2005 | Hitchcock et al. | |
| 7,787,946 B2* | 8/2010 | Stahmann | G16H 20/40 607/3 |
| 7,949,389 B2 | 5/2011 | Wolfberg et al. | |
| 8,313,447 B2 | 11/2012 | Van Leer | |
| 8,378,811 B2 | 2/2013 | Crump et al. | |
| 8,423,298 B2 | 4/2013 | Fernandez | |
| 8,821,415 B2 | 9/2014 | Al-Ali et al. | |
| 8,868,164 B2 | 10/2014 | Kabakov et al. | |
| 9,078,582 B2 | 7/2015 | Tupin, Jr. et al. | |
| 9,125,574 B2 | 9/2015 | Zia et al. | |
| 9,392,952 B1 | 7/2016 | Oz et al. | |
| 9,566,041 B2 | 2/2017 | Christensen et al. | |
| 9,579,055 B1 | 2/2017 | Rood et al. | |
| 9,693,730 B2 | 7/2017 | Workman et al. | |
| 9,736,600 B2 | 8/2017 | Neumeyer et al. | |
| 9,763,583 B2 | 9/2017 | Oz et al. | |
| 9,763,616 B2 | 9/2017 | Dugan | |
| 9,794,526 B2 | 10/2017 | Paula-Molina et al. | |
| 10,278,581 B2 | 5/2019 | Gaster | |
| D866,199 S | 11/2019 | Carlile et al. | |
| D868,978 S | 12/2019 | Carlile et al. | |
| D877,344 S | 3/2020 | Munger | |
| 2007/0077265 A1 | 4/2007 | Klueh et al. | |
| 2010/0305481 A1* | 12/2010 | Igney | A61B 5/6892 600/595 |
| 2012/0059268 A1 | 3/2012 | Tupin, Jr. | |
| 2013/0096440 A1 | 4/2013 | Kiraly | |
| 2014/0180153 A1* | 6/2014 | Zia | A61B 7/00 600/528 |
| 2015/0265204 A1 | 9/2015 | Tupin, Jr. et al. | |
| 2016/0157717 A1 | 6/2016 | Gaster | |
| 2017/0049414 A1* | 2/2017 | Venugopalan | A61B 8/565 |
| 2017/0086709 A1 | 3/2017 | Khine et al. | |
| 2017/0281087 A1 | 10/2017 | Workman et al. | |
| 2018/0000405 A1* | 1/2018 | Penders | A61B 8/4416 |
| 2018/0092564 A1* | 4/2018 | Meriheinä | A61B 5/0006 |
| 2018/0108440 A1* | 4/2018 | Stevens | G06N 3/044 |
| 2018/0317789 A1* | 11/2018 | Ransbury | G16H 40/67 |
| 2018/0336968 A1* | 11/2018 | Hwang | A61B 5/6891 |
| 2019/0142322 A1 | 5/2019 | Lee et al. | |

FOREIGN PATENT DOCUMENTS

| | | | | |
|---|---|---|---|---|
| WO | WO-2018148251 A1 * | 8/2018 | .......... | A61B 5/0205 |
| WO | WO-2019133926 A1 * | 7/2019 | ......... | A61B 5/02411 |

OTHER PUBLICATIONS

Prashanth Chetlur Adithya, Ravi Sankar, Wilfrido Alejandro Moreno, Stuart Hart, Trends in fetal monitoring through phonocardiography: Challenges and future directions, Biomedical Signal Processing and Control, vol. 33, 2017, pp. 289-305, ISSN 1746-8094, https://doi.org/10.1016/j.bspc.2016.11.007. (Year: 2017).*

Bera, Binoy, and Madhumita Das Sarkar. "Piezoelectricity in PVDF and PVDF based piezoelectric nanogenerator: a concept." IOSR J. Appl. Phys 9.3 (2017): 95-99. (Year: 2017).*

A. Bin Queyam, R. Kumar Meena, S. Kumar Pahuja and D. Singh, "An IoT Based Multi-Parameter Data Acquisition System for Efficient Bio-Telemonitoring of Pregnant Women at Home," 2018 8th International Conference on Cloud Computing, Data Science & Engineering (Confluence), Noida, India, 2018, pp. 14-15 (Year: 2018).*

V. A. B. K. Vadali, S. Pandey, P. C. Adithya and R. Sankar, "Fetal Phonocardiogram Decomposition Framework," SoutheastCon 2018, St. Petersburg, FL, USA, 2018, pp. 1-4, doi: 10.1109/SECON.2018.8478991. (Year: 2018).*

J. Oliveira, F. Renna, T. Mantadelis and M. Coimbra, "Adaptive Sojourn Time HSMM for Heart Sound Segmentation," in IEEE Journal of Biomedical and Health Informatics, vol. 23, No. 2, pp. 642-649, Mar. 2019, doi: 10.1109/JBHI.2018.2841197. (Year: 2019).*

\* cited by examiner

FETAL HEALTH MONITORING SYSTEM AND METHOD FOR USING THE SAME

CROSS-REFERENCE TO RELATED APPLICATIONS

This application claims priority to U.S. Provisional Patent Application No. 63/034,146 filed on Jun. 3, 2020, the entire contents of which are incorporated by reference herein.

TECHNICAL FIELD

The present invention relates generally to the field of health monitoring, and particularly to a system and method of monitoring fetal health.

BACKGROUND

Fetal health monitoring, especially in at-risk pregnancies, can contribute positively to maintaining prenatal health of parent and child. Several options exist for in-clinic monitoring, but few are suitable for at-home environments, much less unobtrusive, wearable, continuous monitoring. Common methods for assessing fetal health include ultrasound imaging, fetal Doppler echocardiography, fetal electrocardiography (fECG), cardiotocography, and placental or intravenous biochemical assays. Fetal movement (fM) and fetal heart rate (fHR) measurements are ideal proxies for non-invasively monitoring fetal health. Fetal heart rate variability (fHRV) is commonly used as a diagnostic tool for high-risk pregnancies. Most fetal health diagnostic techniques are ill-suited for long-term use at home due to factors such as bulky equipment, difficulty of use without a technician, and risk to the fetus. Ultrasound, while a staple of clinical patient care, is not viable for home use. Echocardiography is directionally dependent, which can lead to false readings when not applied by a clinician. Literature has suggested that long-term exposure to ultrasound can lead to adverse effects. Accordingly, application of ultrasound outside of a clinical setting is generally discouraged, unless ordered by a physician. There are only a few options available for at-home fetal monitoring. This is due to challenges in both acquiring a suitable fetal biosignal and effectively processing the fetal biosignal once acquired. Fetal biosignals are often contaminated by stronger maternal biosignals, and methods to separate maternal and fetal biosignals with hardware are invasive and not ideal for wearable continuous monitoring.

Accordingly, need exists for a solution that overcomes the above-noted challenges.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

Disclosed herein is a wearable fetal health monitoring device for determining a heath condition of a fetus based on biosignals of an expecting mother and the fetus. In various embodiments, the device comprises: a microelectromechanical system (MEMS) accelerometer that converts an acoustic wave sensed in an abdominal region into an abdominal acoustic signal; a pulse oximeter that generates a maternal photoplethysmogram (mPPG) value from a pulse sensed in the abdominal region; and a microcontroller. The microcontroller is configured to: generate a maternal phonocardiogram (mPCG) value from the abdominal acoustic signal; calculate a first maternal heart rate (mHR) value from the mPCG value; calculate a second mHR value from the mPPG value; compare the first mHR value with the second mHR value to identify a noise correction value; and apply the identified noise correction value to the mPCG value to extract a fetal phonocardiogram (fPCG) value.

In at least one embodiment, the device further comprises at least one of: a memory and a wireless transceiver.

In at least one embodiment, the microcontroller is further configured to calculate from the fPCG value at least one of: a fetal heart rate (fHR) value and a fetal heart rate variability (fHRV) value.

In at least one embodiment, the microcontroller is further configured to calculate a fetal movement (fM) value from the abdominal acoustic signal.

In at least one embodiment, the pulse oximeter is further configured to sense a maternal peripheral capillary oxygen saturation (mSpO2) value.

In at least one embodiment, the MEMS accelerometer comprises at least one of an acoustic wave sensor and a pressure wave sensor.

In at least one embodiment, the microcontroller is further configured to calculate a maternal activity level from at least one of the mPPG value and the first mHR value and the second mHR value.

In at least one embodiment, the device further comprises one or more of: a MEMS inclinometer, an inertia sensor, and a gyroscope.

In at least one embodiment, the device further comprises at least one of: a power source operatively coupled to a wireless transceiver, a memory, and an electrode.

In at least one embodiment, the device further comprises a patch that removably attaches to a maternal torso.

In at least one embodiment, the device further comprises two units spaced apart from each other, wherein the two units are carried on a belt or band that surrounds a maternal torso.

In at least one embodiment, the device further comprises an acoustic impedance matching housing.

In at least one embodiment, the microcontroller is further configured to deconvolute the abdominal acoustic signal using at least one of the first mHR value and the second first mHR value.

In at least one embodiment, the device further comprises an inclinometer sensor that detects a sub-audible abdominal acoustic wave.

In at least one embodiment, a first portion of the device is disposable, and wherein a second portion of the device is re-usable.

In at least one embodiment, the device further comprises a ferroelectric nanogenerator sensor that detects abdominal pressure waves.

In at least one embodiment, the device further comprises a noise attenuator configured to: at least partially constructively or destructively combine a first physiological signal component of a first signal output by a first acoustic sensor and a second physiological signal component of a second signal output by a second acoustic sensor.

Disclosed herein is a method of determining a heath condition of a fetus based on biosignals of an expecting mother and the fetus. In various embodiments, the method comprises providing a wearable fetal health monitoring device. The device comprises: a microelectromechanical system (MEMS) accelerometer that converts an acoustic wave sensed in an abdominal region into an abdominal acoustic signal; a pulse oximeter that generates a maternal photoplethysmogram (mPPG) value from a pulse sensed in the abdominal region; and a microcontroller. The microcontroller is configured to: generate a maternal phonocardiogram (mPCG) value from the abdominal acoustic signal; calculate a first maternal heart rate (mHR) value from the mPCG value; calculate a second mHR value from the mPPG value; compare the first mHR value with the second mHR value to identify a noise correction value; and apply the identified noise correction value to the mPCG value to extract a fetal phonocardiogram (fPCG) value. The method further comprises: generating a maternal phonocardiogram (mPCG) value from the abdominal acoustic signal; calculating a first maternal heart rate (mHR) value from the mPCG value; calculating a second mHR value from the mPPG value; comparing the first mHR value with the second mHR value to identify a noise correction value; and applying the identified noise correction value to the mPCG value to extract a fetal phonocardiogram (fPCG) value.

In at least one embodiment, the method further comprises calculating from the fPCG value at least one of: a fetal heart rate (fHR) value and a fetal heart rate variability (fHRV) value.

In at least one embodiment, the method further comprises outputting at least one of a normal state, caution state, and emergency state based on the extracted fetal phonocardiogram (fPCG) value.

In at least one embodiment, the method further comprises calculating a fetal movement (fM) value from the abdominal acoustic signal.

DETAILED DESCRIPTION

Figure 1A:
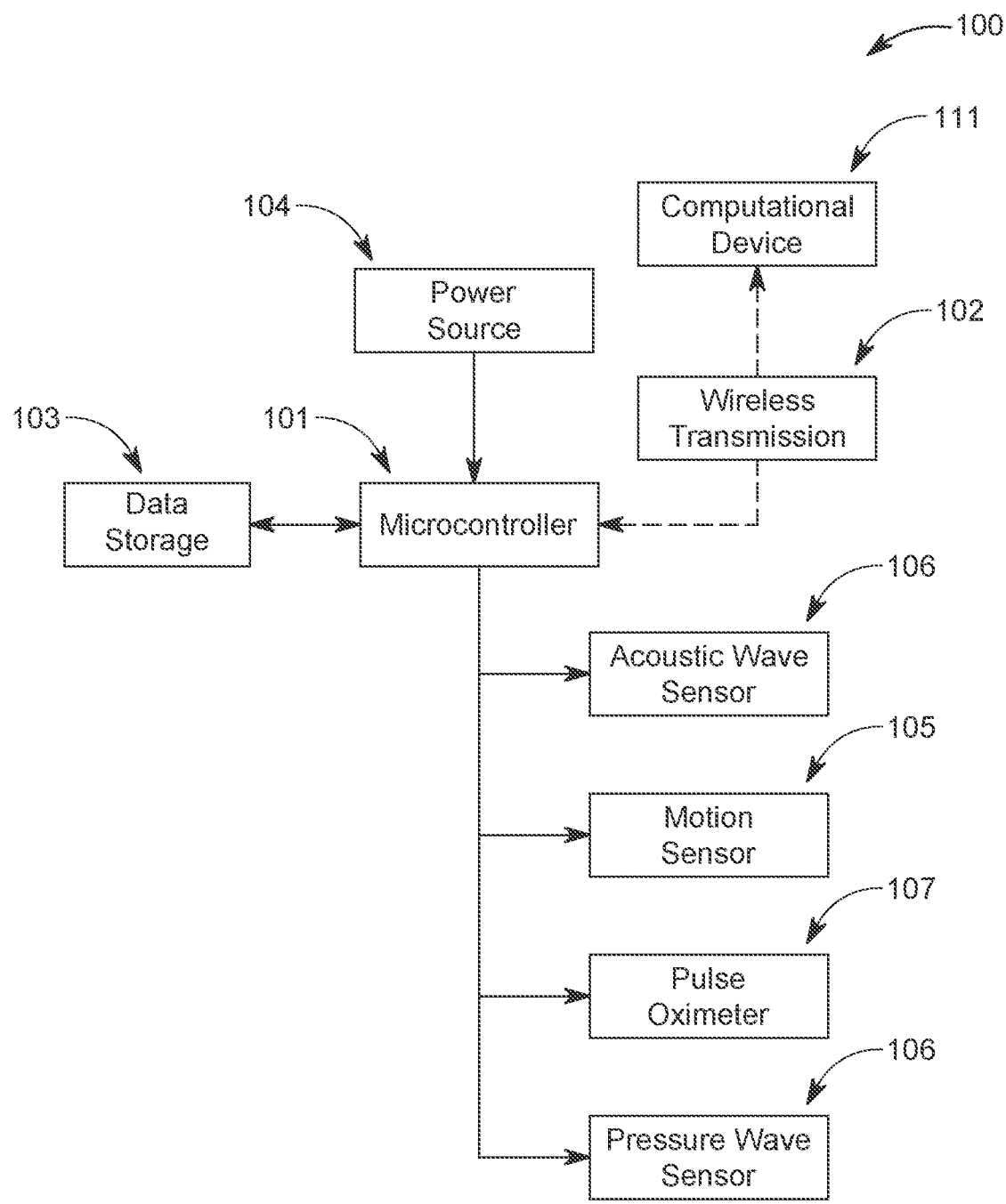
FIG. 1A is a block diagram of the hardware in a fetal monitoring device, according to at least one embodiment of the presently disclosed subject matter.
Figure 1B:
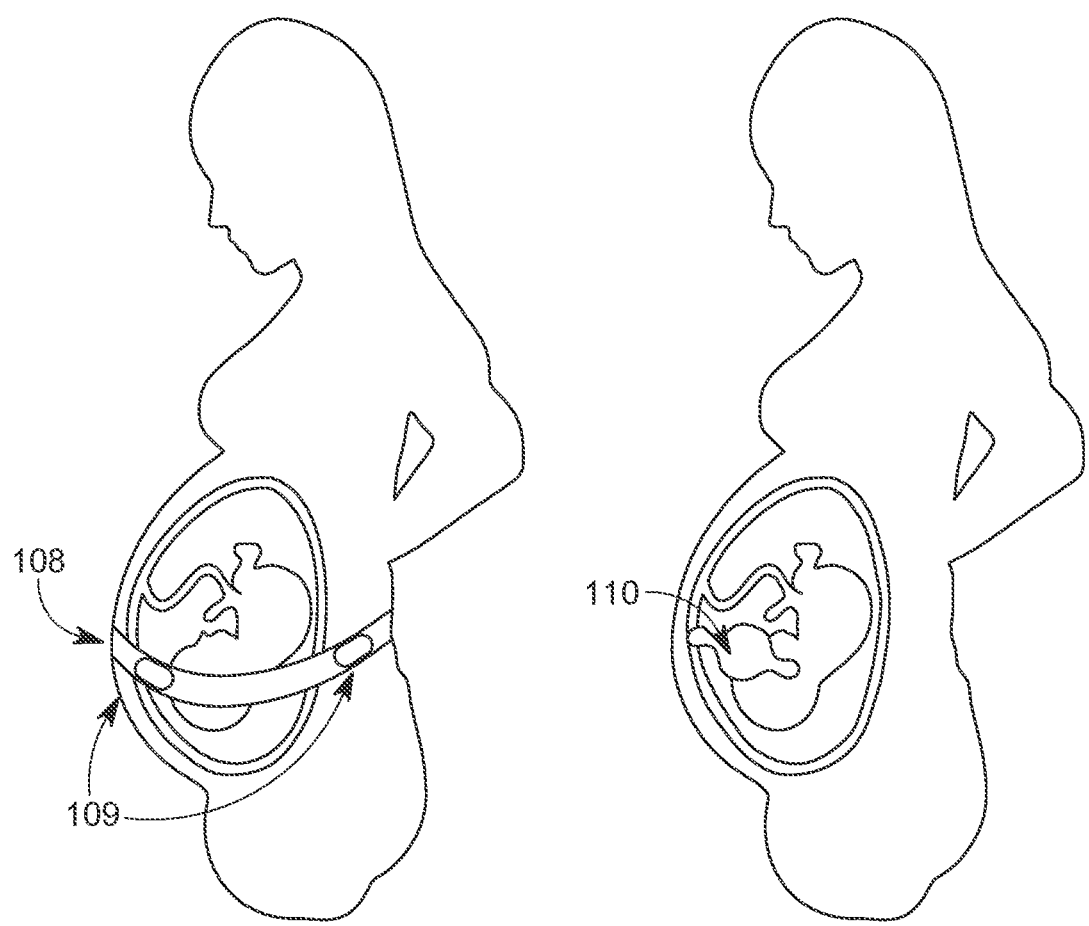
FIG. 1B is a perspective view illustrating placement of a belt-based version of the fetal monitoring device as well as an adhesive patch version of the fetal monitoring device, according to at least one embodiment of the presently disclosed subject matter.

The following description and drawings are illustrative and are not to be construed as limiting. Numerous specific details are described to provide a thorough understanding of the disclosure. However, in certain instances, well-known or conventional details are not described in order to avoid obscuring the description. Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

There are few viable options available for at-home fetal monitoring due to challenges in both acquiring a suitable fetal biosignal and effectively processing the fetal biosignal once acquired. Fetal biosignals are often contaminated by stronger maternal biosignals, and methods to separate maternal and fetal biosignals with hardware are invasive and not ideal for wearable continuous monitoring. Embodiments of the presently disclosed subject matter overcome limitations existing in the art by way of innovative applications of hardware and signal processing techniques.

Fetal movement (fM), fetal heart rate (fHR), and fetal heart rate variability (fHRV) are clinically proven indicators of fetal health, and can be used for making diagnostic decisions, especially when combined with maternal biosignals. Embodiments of the presently disclosed subject matter provide for these biosignals to be transduced acoustically and non-invasively without exposing the fetus to excess ultrasound. Embodiments of the presently disclosed subject matter provide for a small wearable device that may combine features such as: acoustic wave sensors, motion sensors, an acoustic impedance matching housing, optical sensors coupled to a microcontroller, a data storage module, a wireless communication module, and a power source. By provision of such features, it can be possible to transduce several biosignals, including: fM, abdominal phonocardiogram (aPCG), maternal photoplethysmogram (mPPG), and maternal peripheral capillary oxygen saturation (mSpO$_2$). Source separation algorithms are implemented to distinguish the fetal phonocardiogram (fPCG) and fM from other components of the aPCG. For robustness, in on embodiment, the maternal heart rate (mHR) calculated from the maternal phonocardiogram (mPCG) may be compared to the mHR calculated from the mPPG for noisy signal rejection. In on embodiment, a feature extraction algorithm forming of the embodiment, utilizes novel methods of signal processing and machine learning for identifying individual fetal heartbeat components. In at least one embodiment, a second feature extraction algorithm operates to identify individual fetal movement events. In at least one embodiment, a diagnostic algorithm determines fetal condition from fM, fHR, fHRV, and mSpO2 calculated from the extracted features.

Fetal Phonocardiography (fPCG) is often a secondary tool that provides very important information about fetal well-being that cannot be given by another fetal monitoring method. Independent Component Analysis (ICA) and Principal Component Analysis (PCA) are often chosen for testing on synthetic data that are able to extract fPCG from abdominal signals. Results show that ICA and PCA could be used in clinical practice for fetal Heart Rate (fHR) monitoring, due to reducing the complexity for determining fHR.

Figure 2:
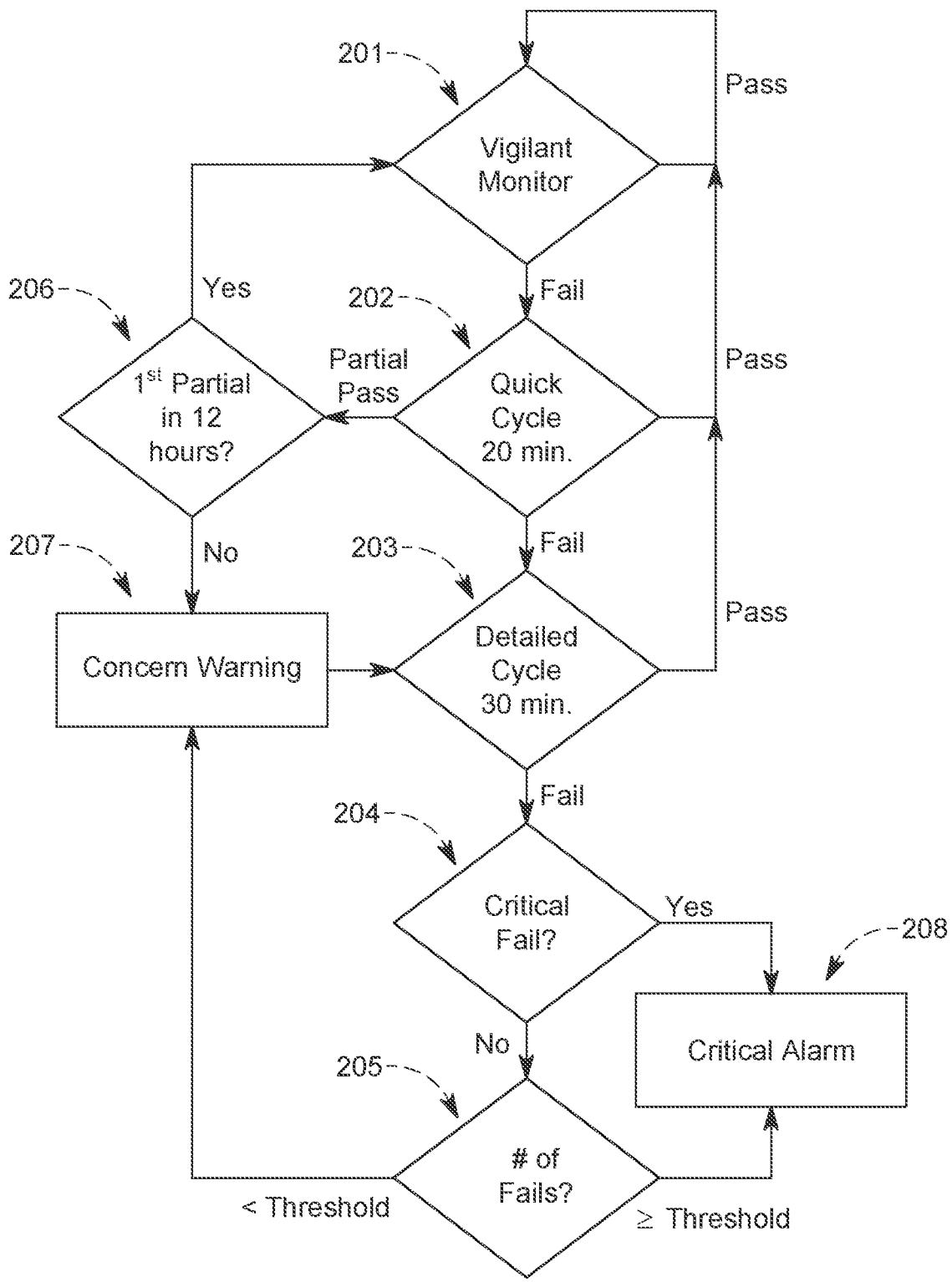
FIG. 2 is a flowchart of an operational cycle of the fetal monitoring device, according to at least one embodiment of the presently disclosed subject matter.
Figure 3A:
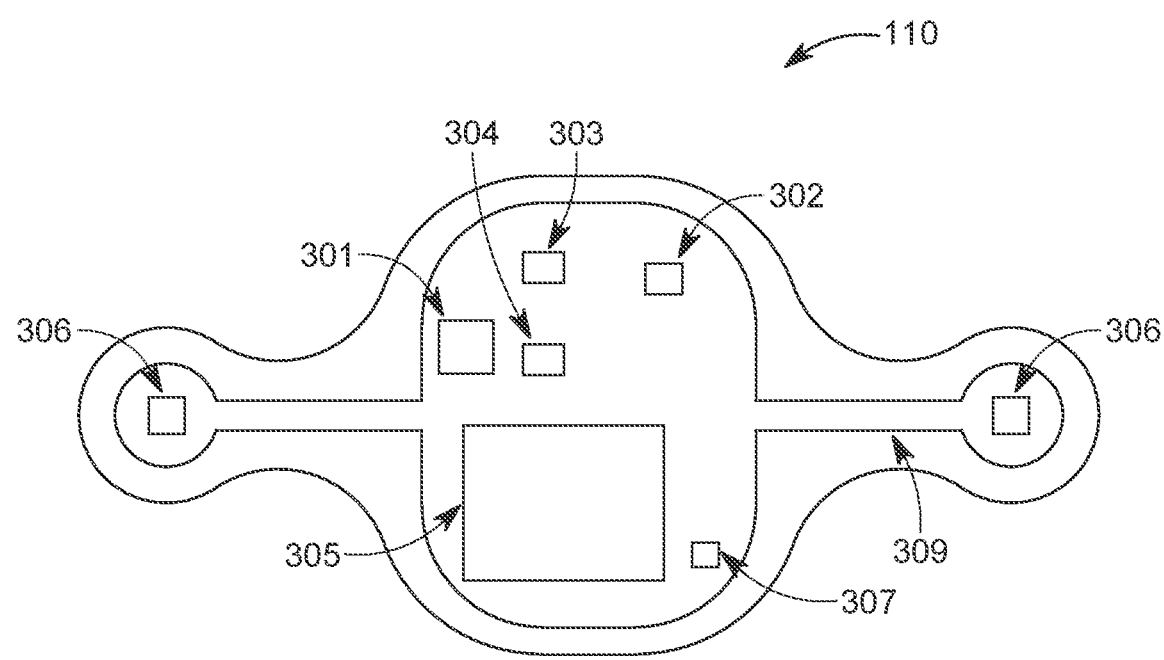
FIG. 3A is a top-down view of a non-contact side of a fetal monitoring patch, according to at least one embodiment of the presently disclosed subject matter.
Figure 3B:
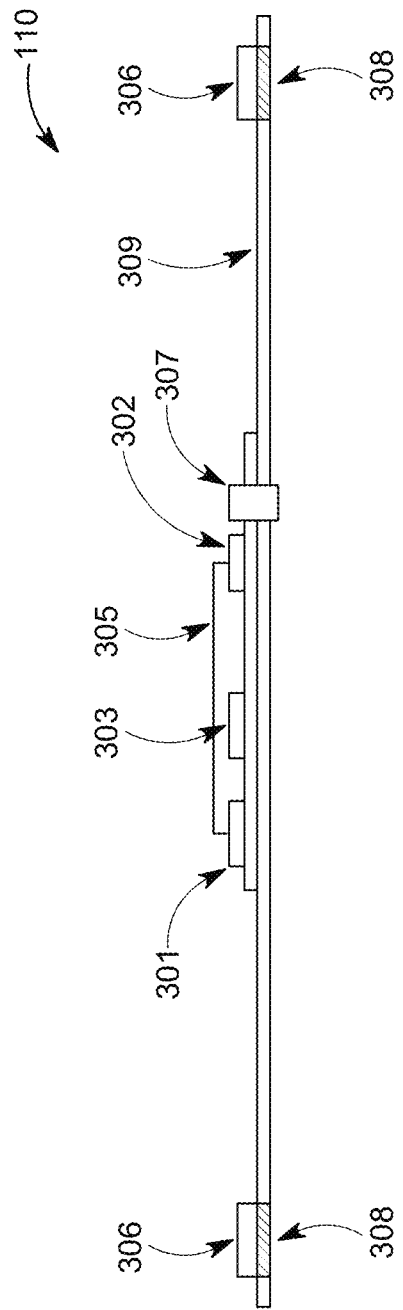
FIG. 3B is a profile view of internal components of the fetal monitoring patch, according to at least one embodiment of the presently disclosed subject matter.
Figure 3C:
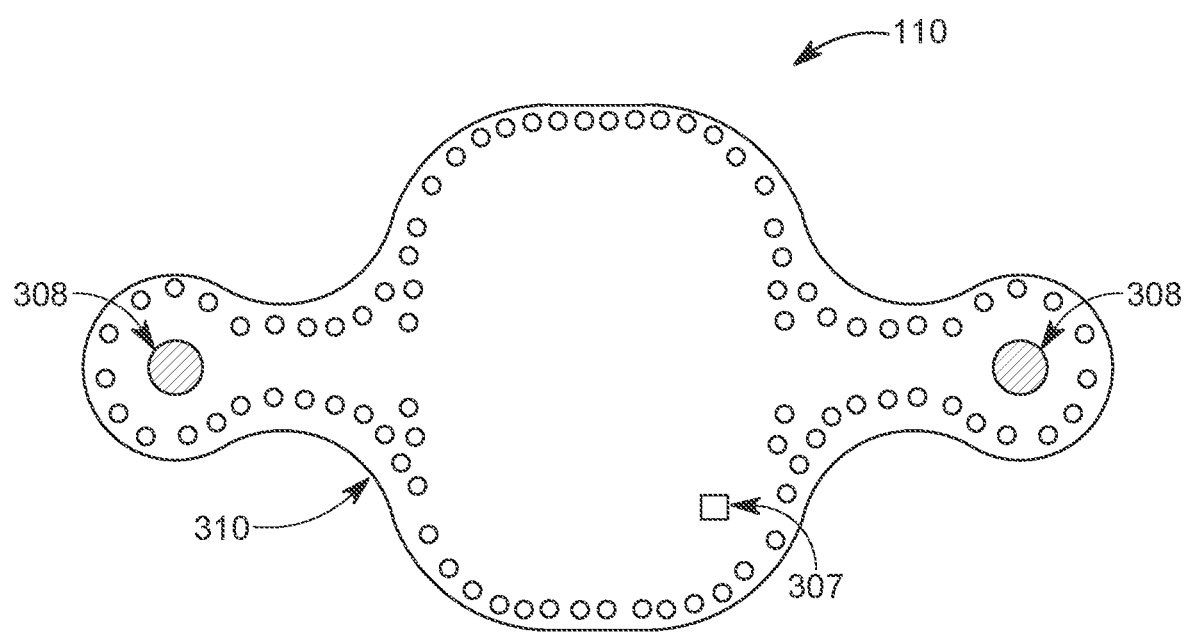
FIG. 3C is a bottom view of the skin contacting side of the fetal monitoring patch, according to at least one embodiment of the presently disclosed subject matter.
Figure 3D:
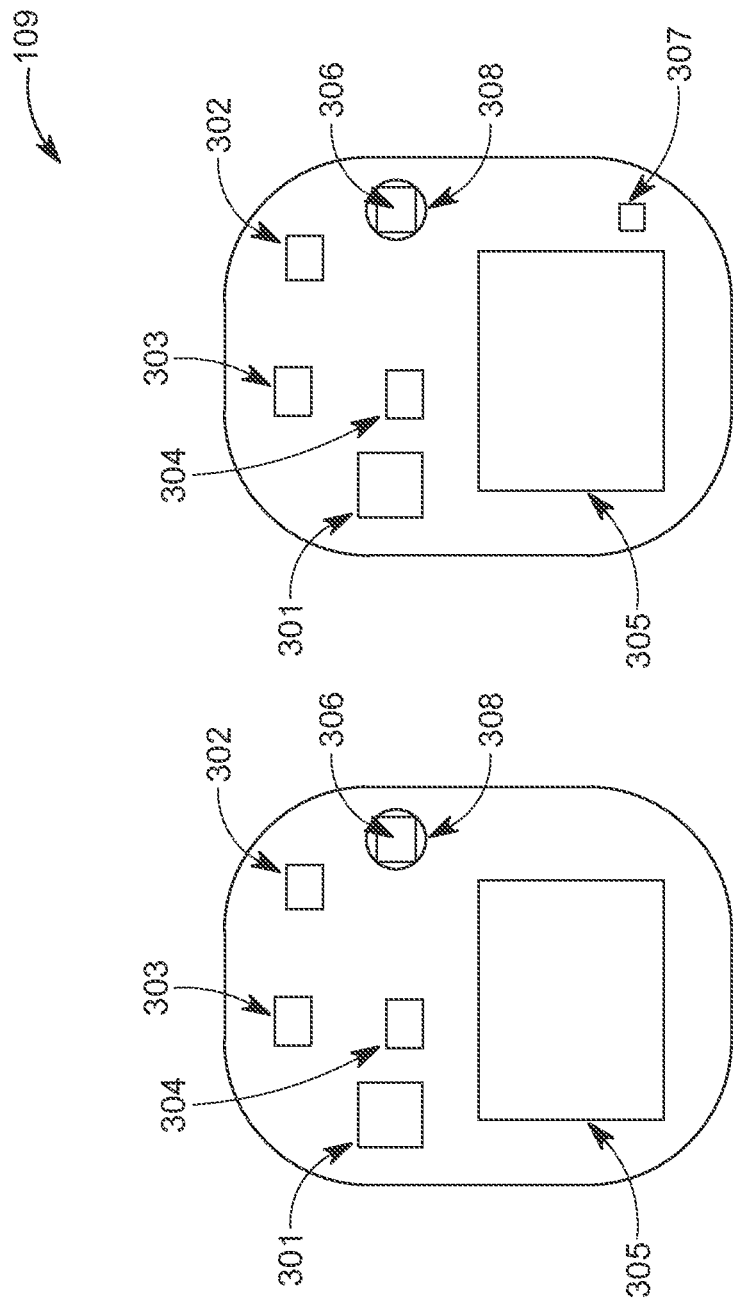
FIG. 3D is a top-down view of the two hardware modules of the fetal monitoring band, according to at least one embodiment of the presently disclosed subject matter.
Figure 4:
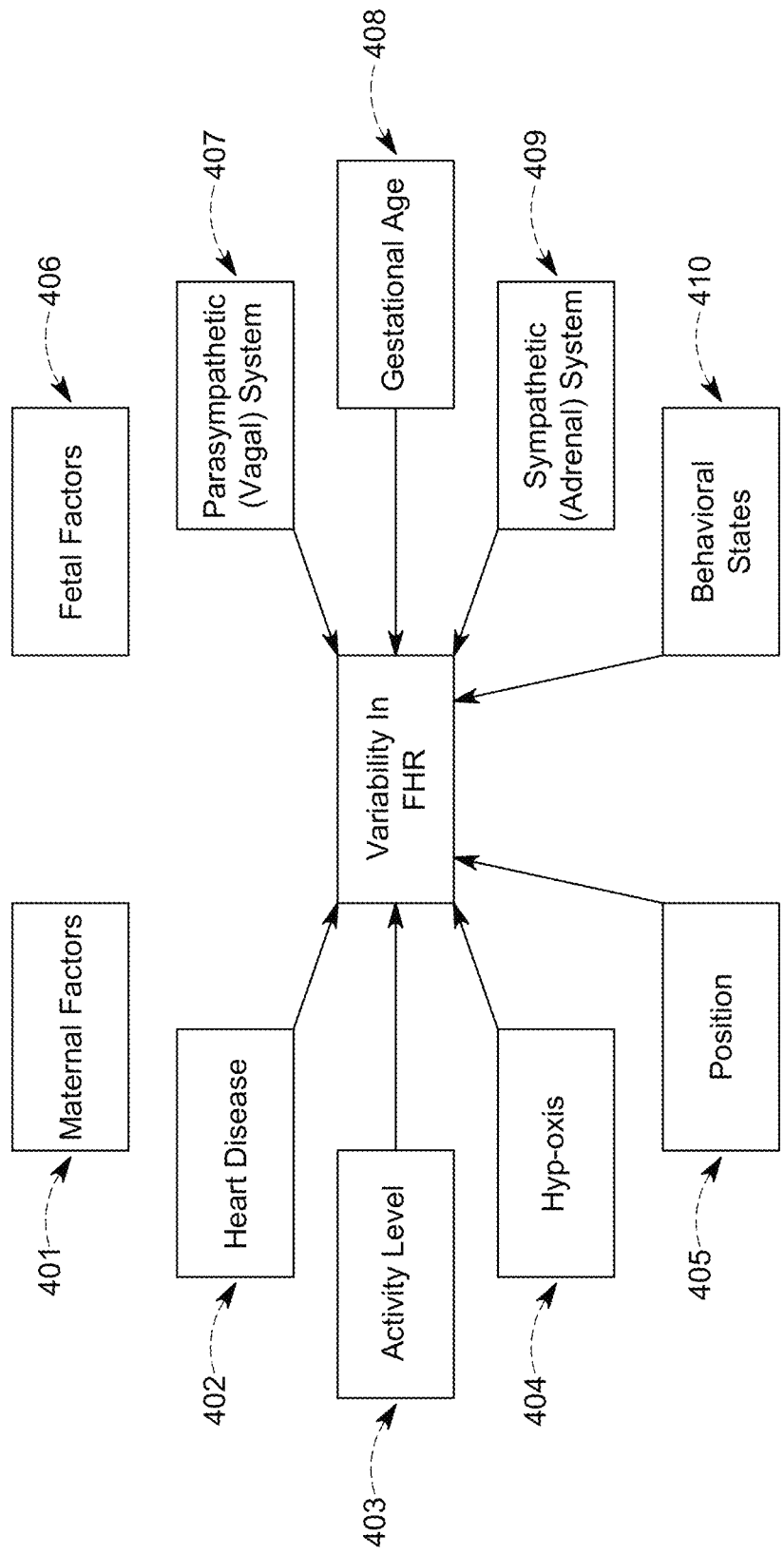
FIG. 4 is a descriptive figure of primary influences on fetal heart rate variability, according to at least one embodiment of the presently disclosed subject matter.
Figure 5:
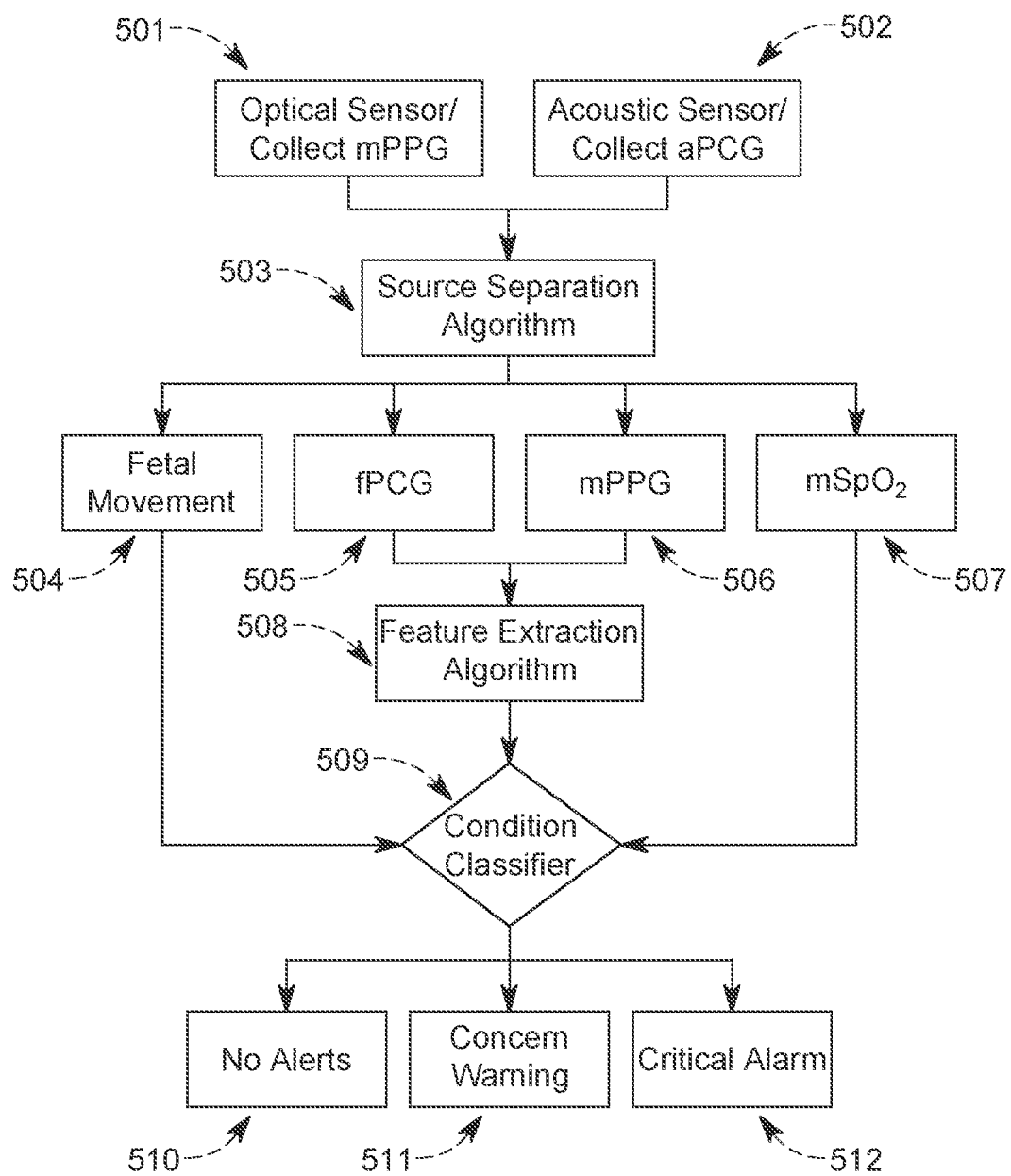
FIG. 5 is a flowchart of the flow of data in the fetal monitoring device, according to at least one embodiment of the presently disclosed subject matter.
Figure 6:
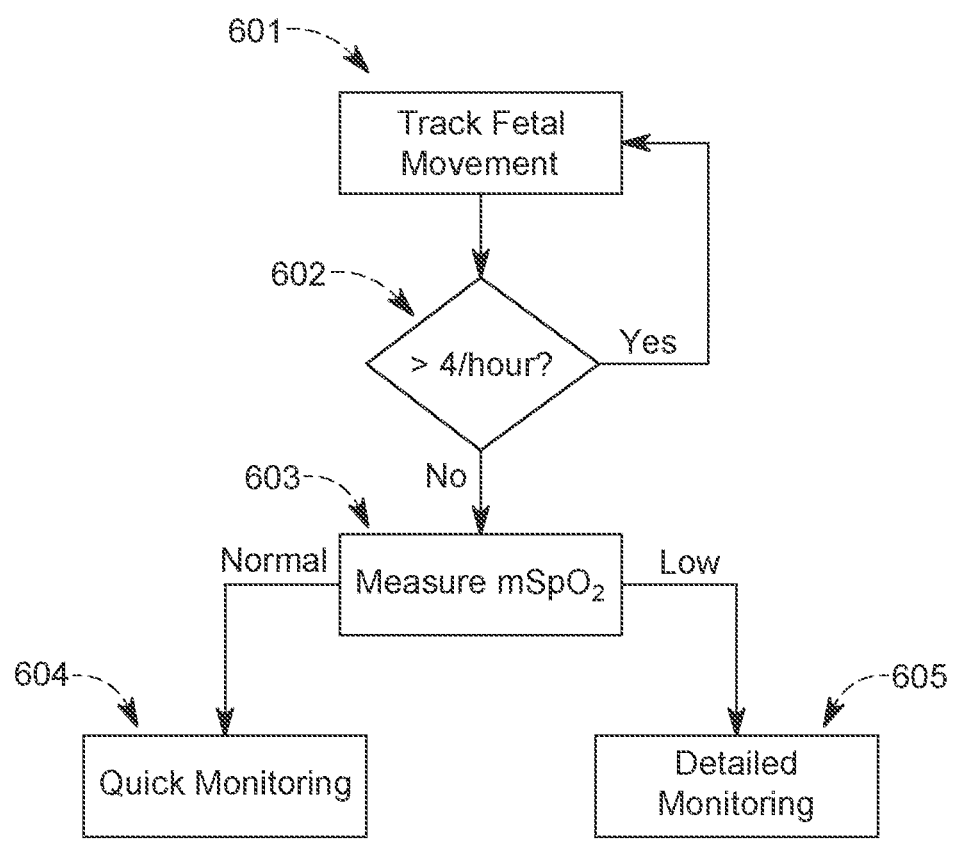
FIG. 6 is a flowchart of the vigilant monitor decision stream, according to at least one embodiment of the presently disclosed subject matter.

FIGS. 1 through 6 illustrate various aspects of the presently disclosed subject matter. FIG. 1A is a block diagram of various physical hardware in a wearable fetal monitoring device, according to at least one embodiment of the presently disclosed subject matter. FIG. 1B is a perspective view illustrating the placement of the belt-based version of the device and the adhesive patch version of the device, according to at least one embodiment of the presently disclosed subject matter. FIG. 2 is a flowchart of the operational cycle of a fetal monitoring device, according to at least one embodiment of the presently disclosed subject matter. FIG. 3A is a top-down view of the non-contact side of a fetal monitoring patch, according to at least one embodiment of the presently disclosed subject matter. FIG. 3B is a profile view of the internal components of a fetal monitoring patch, according to at least one embodiment of the presently disclosed subject matter. FIG. 3C is a bottom view of the skin contacting side of a fetal monitoring patch, according to at least one embodiment of the presently disclosed subject matter. FIG. 3D is a top-down view of the two hardware modules of a fetal monitoring band, according to at least one embodiment of the presently disclosed subject matter. FIG. 5 is a flowchart of the flow of data in a fetal monitoring device, according to at least one embodiment of the presently disclosed subject matter. FIG. 6 is a flowchart of a vigilant monitor decision stream, according to at least one embodiment of the presently disclosed subject matter.

FIG. 1A illustrates an exemplary hardware system for non-invasive, continuous fetal health monitoring. In various embodiments, a fetal health monitoring device (alternately referred to herein as "device") as provided herein is configured to determine heath of a fetus based on biosignals of an expecting mother and her fetus. In at least one embodiment, the device is a wearable device. The device as disclosed herein may be integrated within a system such as system 100 that is further disclosed herein. According to at least one embodiment, system 100 includes a microcontroller 101 that performs tasks such as executing commands, collecting input from sensors, and communicating with a user. In at least one embodiment, microcontroller 101 operates to transmit raw signals through a bidirectional wireless communication channel such as wireless transmission 102 to an external computational device such computational device 111. Wireless transmission 102 may comprise low power data transfer protocols including, but not limited to, Bluetooth LE, NFC, mesh, Zigbee, and similar other low power data transfer protocols commonly known in the art. In at least one embodiment, the system includes a high-speed data storage or memory unit such as data storage 103. Data storage 103 may be used for signal processing onboard the wearable device without wireless transmission. In one embodiment, signal processing will be done in combination of onboard and external computational devices as dictated by power constraints. System 100 can further include a power source 104 provided, for example, in the form of a battery, wireless power transfer, super capacitor, or a similar other mechanism. Information on internal abdominal movement may be collected via a motion sensor 105. In various embodiments, motion sensor 105 may take the form of a low-frequency microelectromechanical system (MEMS) accelerometer, MEMS inclinometer, inertia sensor, or gyroscope. Abdominal acoustic signal may be transduced through an acoustic wave sensor 106. In various embodiments, acoustic wave sensor 106 may take the form of a MEMS accelerometer, MEMS inclinometer, inertia sensor, or a gyroscope. In at least one embodiment, acoustic wave sensor 106 may be replaced with one or more pressure wave sensors that includes a capacitive diaphragm or a ferroelectric nanogenerator pressure sensor. In various embodiments, the hardware provided on the device forming part of system 100 advantageously does not require the external measurement of quantities such as electrical potential or current flux to acquire the fetal signal. In some embodiments, the fetal health monitoring device forming part of system 100 is configured as belt-based sensing units 109 mounted on a belt 108, as shown on the left side illustration of FIG. 1B. In various embodiments, belt 108 may comprise a breathable elastomeric or fabric material. In some embodiments, the device forming part of system 100 is configured as a singular unit in the form of a wearable pressure adhesive patch in the form of patch 110, as shown on the right-side illustration of FIG. 1B.

In at least one embodiment, the fetal health monitoring device forming part of system 100 may operate through an operational decision-making cycle shown in FIG. 2. Various aspects of vigilant monitoring 201 are explained further by way of a flowchart illustrated in FIG. 6. According on one embodiment, vigilant monitor 201 may run continuously unless a "fail" condition occurs. The "fail" condition may include instances such as, for example, less than 4 fM events detected per hour, a low mSpO$_2$ condition, or a similar other situation that indicates that the health of the fetus may be negatively impacted. In response to such a "fail" condition, the device and/or system may transition to conduct a quick interrogation cycle such as quick cycle 202. In one embodiment, the quick interrogation cycle by way of quick cycle 202 may average twenty (20) minutes in length; in this embodiment, the average of twenty (20) minutes may be needed to draw physiologically relevant conclusions. Quick cycle 202 may proceed to investigate fHR and accelerations in fHRV. FIG. 4 illustrates the primary influences on (i.e., the various factors that may cause, impact or affect) Fetal heart rate variability (fHRV).

Quick cycle 202 may return the device/system back to the low-power vigilant monitoring state (i.e., to vigilant monitor 201) when one or more of the following exemplary conditions are met: no bradycardia, no tachycardia, and adequate accelerations of 12-15 bpm above baseline twice in twenty (20) minutes or once with fM. A partial pass is considered brief periods of minor bradycardia or tachycardia, or inadequate acceleration intensity or frequency 10-12 bpm above baseline or once in twenty (20) minutes. If the condition of $1^{st}$ partial pass in 12 hours 206 is met, vigilant monitoring will resume; if the condition is not met, a concern warning 207 is generated, followed by a detailed interrogation cycle (such as detailed cycle 203) is initiated by the device/system. In one embodiment, detailed cycle 203 runs for a minimum of thirty (30) minutes, and investigates fHRV, fM, and $mSpO_2$ in more detail. Detailed cycle 203 pass conditions may include the same conditions as those required for passing quick cycle 202 in addition to no erratic or spontaneous fetal cardiac decelerations. In at least one embodiment, the frequency and duration of acceleration events may be set to equal to or larger than a baseline from a prior week. A critical failure condition such as critical fail 204 is established if any of the following is true: sustained tachycardia or bradycardia, a distinct lack of variability that meets minimum requirements, a significant reduction in frequency or duration of acceleration events when compared to weekly values. A critical failure triggers a critical alert 208. On the other hand, a general failure triggers number of fails 205 module that performs a comparison by first counting a number of detailed cycle 203 failures since a last pass. If number of fails counted is less than three (3), a concern warning is sent by the device/system, and another detailed cycle 203 is commenced. In at least one embodiment, the occurrence of three consecutive non-critical failures within a 90-minute time interval triggers critical alert 208. According to at least one embodiment, at startup of the device and at least once per day, the device runs the quick cycle 202 interrogation for calibration and as a manner of maintaining weekly records (or records at other predetermined time periods) for longitudinal monitoring requirements in the diagnostic algorithm.

In various embodiments, the physiological values used for determining pass/fail state transitions may be configured to be adjustable based on a gestational age determined for the user (e.g., the wearer) and other parameters input during initial device setup. In one embodiment for a telemedicine application, a physician may determine or control the physiological values as well as a frequency of diagnostic cycles. In one embodiment, the user (e.g., the wearer of the device) can begin a diagnostic cycle through the user interface. In one embodiment, the user is able to adjust the physiological numbers as well as the frequency of diagnostic cycles.

In at least one embodiment, the operational decision-making cycle as shown in FIG. 2 further includes a warning such as concern warning 207. Concern warning 207 may include an audio and/or visual user notification of an abnormal reading with a potential cause of the reading. Several consecutive warnings may signal/notify the user or otherwise encourage the user to schedule an obstetrician (OB) visit. Concern warnings will be structured to be informative without causing undue concern as rising stress levels may contaminate future readings.

In at least one embodiment, the operational decision-making cycle as shown in FIG. 2 further includes an alert such as critical alert 208. Critical alert 208 may notify the user to call an emergency medical hotline or make an emergency clinical visit. In a telemedicine embodiment, an alert will be sent to a monitoring clinician. In a shared user embodiment, an alert can be sent to other authorized access holders.

A simplified component layout of a wearable fetal monitoring device in the form of a wearable pressure adhesive patch 110 (alternately referred to herein as "patch 110" or "patch") is shown in FIGS. 3A, 3B and 3C. FIG. 3A illustrates a nondermal distal side of patch 110 with primary components visible. In one embodiment, components of patch 110 are placed on a flexible board and connected with one or more flexible interconnects 309. The components of patch 110 can comprise a microcontroller 301. In one embodiment, microcontroller 301 can comprise one of one or multiple cores capable of ultralow power sleep states. The components of patch 110 can further comprise a wireless communication module 302. In one embodiment, wireless communication module 302 can comprise one or more of the following sub-components: chip antenna, rigid-island antenna, flexible antenna, and similar other sub-components. The components of patch 110 cab furthermore comprise a memory data storage 303. In one embodiment, memory data storage 303 can comprise a non-volatile memory data storage such as, for example, a Quad-SPI non-volatile memory data storage. The components of patch 110 can additionally comprise power management circuit 304 and a power source 305. In one embodiment, patch 110 includes a breathable substrate 310. In one embodiment, a biocompatible material engineered to match the acoustic impedance of soft tissue is shown in the dermal contact side of patch 110. In one embodiment, patch 110 further includes an acoustic impedance coupler 308. In one embodiment, acoustic impedance coupler 308 is the primary point of skin contact for acoustic sensors 306 to minimize reflected signal loss due to acoustic impedance mismatch between the fetal health monitoring device and soft tissue. Since, the fetal signal is generally low magnitude, maximizing signal transmission to transducer is key for accurate feature extraction. The material in acoustic impedance coupler 308 can be composed of polydimethylsiloxane adjusted with $TiO_2$ nanoparticles. In another embodiment, material of acoustic impedance coupler 308 can be composed of modified polyurethane or other nanocomposites.

As shown in FIG. 3B and FIG. 3C, for example, in one embodiment, the only contact points between dermis and patch 110 may exist at pulse oximeter module 307 and one or more acoustic impedance couplers 308. the rest of the patch 110 surface may be isolated from the body or dermis by breathable substrate 310.

A simplified component layout of a wearable fetal monitoring device in the form of belt-based sensing units 109 (alternately referred to herein as "unit 109") is shown in FIG. 3D. In one embodiment, the belt-based sensing unit 109 illustrated in FIG. 3D is similar in construction as patch 110 but splits the acoustic sensors across two units 9 with only one unit 9 having a pulse oximeter module 307. These units 9 may be housed in a belt such that contact is limited to the acoustic impedance coupler 308 and pulse oximeter module 307.

FIG. 4 is a descriptive figure of the primary influences on fetal heart rate variability (fHRV), according to at least one embodiment of the presently disclosed subject matter. The primary influences on fHRV include maternal factors 401. Maternal factors 401 may comprise, for example, heart disease 402, activity level 403, hypoxia 404, and position 405, associated with the user or expectant mother. The primary influences on fHRV further includes fetal factors 406. Fetal factors 406 may comprise, for example, parasympathetic (vagal) system 407, gestational age 408, sympathetic (adrenal) system 409, and behavioral states 410, associated with the fetus.

FIG. 5 is a flowchart of the flow of data/signal associated with a fetal monitoring device, according to at least one embodiment of the presently disclosed subject matter; FIG. 5 is accordingly a flowchart illustrating signal processing flow. Optical sensor 501 includes a pulse oximeter module for collection mPPG. Optical sensor 501 and/or the pulse oximeter module forming part of optical sensor 501 may transduce $mSpO_2$ 507 and mPPG 506.

Acoustic sensor 502 operates to transduce abdominal sounds sensed at an abdominal phonocardiogram (aPCG). In at least one embodiment, an abdominal acoustic signal passes through source separation algorithm 503. Source separation algorithm 503 decomposes the abdominal acoustic signal using the maternal heart rate information obtained by optical sensor 501. During low-power vigilant monitoring state (e.g., during vigilant monitor 201) and during quick interrogation cycle (e.g., during quick cycle 202), a low-fidelity source separation algorithm may be used for signal extraction, including band pass filtering, empirical mode decomposition (EMD), and clustering of intrinsic mode functions (IMF) by signal type. In one embodiment, the IMFs may be selectively recombined into signals such as fetal movement signal (i.e., fM 504) and fetal phonocardiogram signal (i.e., fPCG 505). In detailed interrogation mode of detailed cycle 203, a high-fidelity source separation algorithm is used. The high-fidelity source separation algorithm may include technics such as bandpass filtering, short-time Fourier transform of the abdominal acoustic signal, and audio source separation using a deep neural network generated soft mask. The detailed interrogation mode of the detailed cycle 203 may use these high-fidelity source separation algorithm technics to remove or separate maternal phonocardiogram and abdominal signals. Subsequently, fM and fPCG are separated using empirical mode decomposition EMD. In vigilant monitoring state (e.g., at vigilant monitor 201), after signal acquisition and source separation, fM 504 and $mSpO_2$ 507 are sent to a condition classifier algorithm to determine a pass/fail state discussed in FIG. 2.

In either interrogation mode (i.e., in the quick interrogation cycle such as quick cycle 202, or in the detailed interrogation cycle such as detailed cycle 203), fPCG 505 and mPPG 506 are sent to a feature extraction algorithm 508. Feature extraction algorithm 508 operates to first determine important peaks through homomorphic envelograms and Hilbert-Huang transformation. After smoothing and spike removal, peaks are segmented using a duration-dependent hidden Semi-Markov Model (DD-HSMM) into relevant cardiac states, first heart sound ($S_1$), second heart sound ($S_2$), systolic silence, and diastolic silence. The DD-HSMM is trained with clinical data to segment a signal based on the limited physiological duration of fetal cardiac states. After extraction and annotation, fHRV is calculated and passed to the condition classifier 509. Additional details regarding the output states of the condition classifier algorithm including output states such as—no alerts 510, concern warning 511, and critical alarm 512 are described earlier with regard to FIG. 2.

In various embodiments, the user interface on the fetal health monitoring device can include several input buttons, at least one audio piezoelectric buzzer, and at least one visual alert in the form of light emitting diodes (LEDs). In one embodiment, system 100 further includes an application (e.g., a mobile application) configured to display, on the user interface of the computing device, various parameters sensed by the fetal health monitoring device. In one embodiment, primary interaction with the fetal health monitoring device is accomplished through the application operating on one or more of: the device and a computing device such as a mobile computing device.

The application (alternately referred to herein as "mobile app") enables a user the ability to monitor and track the health condition related to the user and the fetus. In one embodiment, the application may also advantageously permits effective communications using the built-in new age tools provided by the application, the application facilitating seamless communications between the user and the user's caregiver, pharmacy, doctor and/or any other stakeholders involved in tracking and improving a health state of the user and the fetus. In one embodiment, the application executes on a computing device (e.g., a cell) owned or operated by the user. In at least one embodiment, system 100 further includes a server that is communication with the application. In at least one embodiment, various software components of system 100 may reside across, the fetal health monitoring device, the computing device on which the application executes, and on the server. In at least one embodiment, system 100 further includes a cloud computing infrastructure. In one embodiment, the application may receive the data from the fetal health monitoring device (e.g., in the form of sensing units 109 or patch 110) either wirelessly or through a wired connection. In one embodiment, the computing device is a smart phone. The application may store, and/or transfer information or data sensed by the fetal health monitoring device to the cloud computing infrastructure and/or the server. The application may advantageously alert a user and/or a healthcare provider associated with the user regarding any relevant alerts, alarms or push notifications.

In one embodiment, the application may be configured to receive push notifications irrespective of whether the mobile application is running in the foreground or in the background of the user's mobile device. In a further embodiment or in the same embodiment, the application may be configured to receive push notifications event when the application is closed (i.e., terminated) in the user's mobile device. The application may further provide the user, or a healthcare provider associated with the user, with the ability to turn on or off an audible alert associated with a push notification. The application may also include a setting page wherein the user may be able to adjust all settings associated with the application.

In one embodiment, primary interaction with the fetal health monitoring device is accomplished through an application operating on the fetal health monitoring device, and on a computing device such as a smart phone, laptop, tablet or a similar other device. In one embodiment, primary interaction with the fetal health monitoring device is accomplished through an application operating only on the fetal health monitoring device, but not on a computing device such as a smart phone; this embodiment eliminates the need for a computing device for system 100 to perform as intended.

In one embodiment, primary interaction is accomplished through a base station for an embodiment that does not include a PDA, computer, or smartphone. The base could be limited to charging or used as an off-board data processing device for users without a smart device.

FIG. 6 is a flowchart illustrating various aspects of one implementation of vigilant monitoring performed by vigilant monitor 201 shown in FIG. 2. According to one embodiment, a primary mode of operation of vigilant monitor 201 comprises checking of fetal movement at track fetal movement 601. When vigilant monitor 201 determines that fetal movement has been sensed greater than 4 times within an hour at decision step 602, vigilant monitor 201 causes the algorithm to repeat checking of fetal movement at track fetal movement 601. If it is determined that fetal movement is sensed only 4 times or less within an hour at decision step 602, vigilant monitor 201 causes the algorithm to commence measuring $mSpO_2$ level at step 603. If at step 603, the $mSpO_2$ level is found to be normal, vigilant monitor 201 causes the algorithm to proceed to quick monitoring at step 604; however, if at step 603, the mSpO2 level is found to be low, vigilant monitor 201 causes the algorithm to proceed to detailed monitoring at step 605.

Embodiments of the present invention may comprise or utilize a special-purpose or general-purpose computer system that includes computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments of the invention can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the invention may be practiced in a cloud-computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Some embodiments, such as a cloud-computing environment, may comprise a system that includes one or more hosts that are each capable of running one or more virtual machines. During operation, virtual machines emulate an operational computing system, supporting an operating system and perhaps one or more other applications as well. In some embodiments, each host includes a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

The power source may include a rechargeable and/or replaceable battery. In these cases, access to the power source, which may be partially or completely removable, is preferably provided by an opening in the garment, or a conductive portion, such as a conductive fiber or patch woven into the garment. Alternatively, the power source may be discarded with the system upon depletion of its energy reserve without requiring access thereto for recharge or replacement. In order to conserve energy, the transmitter is preferably activated and transmits signals to the receiver in response to being worn, such as by detecting pressure or temperature, or selection of an externally accessible switch.

In various embodiments, a wearable system for intrapartum monitoring of fetal health comprised of at least some of the following: a band, wherein the band may comprise one of a semi-disposable or recyclable patch or a thin elastomeric band to be worn on the maternal torso pressing one or more sensing units against the torso; and a maternal pulse oximeter engaged with the band for collecting maternal heartbeat and capillary oxygen saturation information. One or more inclinometers collect low frequency abdominal acoustic wave information. One or more accelerometers collect mid frequency abdominal acoustic wave information. One or more acoustic sensors collect fetal health audio information. AN acoustic impedance matching housing for sensor coupling is provided. A wired power source is provided. The wired power source is operatively coupled to the wireless transmitter and integrated with the material, the system being configured to be worn with the electrode, transmitter, and power source integrated therewith, and wherein the wireless transmitter, electrode and power source are inseparable from the system. A wireless power source is provided. The wireless power source is operatively coupled to the wireless transmitter and integrated with the material, the system being configured to be worn with the electrode, transmitter, and power source integrated therewith, and wherein the wireless transmitter, electrode and power source are inseparable from the system.

In some embodiments, the system further comprises: a noise attenuator hardware or method coupled to acoustic sensor and the noise attenuator configured to: at least partially constructively combine a physiological signal component of a first signal output by the first acoustic sensing element and a physiological signal component of a second signal output by the second acoustic sensing element; and at least partially destructively combine a noise component of the first signal output by the first acoustic sensing element and a noise component of the second signal output by the second acoustic sensing element, which can be processed with the optical signal input from the maternal sensor.

In some embodiments, the system further comprises MEMS accelerometer sensing units for detecting audible range abdominal acoustic waves. In some embodiments, the system further comprises diaphragm or ferroelectric nanogenerator sensing units for detecting abdominal pressure waves. In some embodiments, the wearable system is a thin-film patch. In some embodiments, portions of the wearable system are disposable, and portions are re-usable. In some embodiments, the noise attenuator comprises at least one of: circuitry including an amplifier, a signal processor, or a general—purpose processor.

In some embodiments, the noise attenuator is further configured to generate a reduced noise signal based on constructively combining the physiological signal components and destructively combining the noise components with the maternal physiological signals. In some embodiments, the maternal pulse oximeter sensors are configured to detect maternal activity level, and maternal heartbeat data is used to deconvolute abdominal acoustic wave information. In some embodiments, the system further comprises inclinometer sensing units for detecting sub-audible abdominal acoustic waves.

In some embodiments, a computer implemented method using the system is provided. The method is for determining fetal seismocardiography data from abdominal acoustic wave data obtained through inclinometer sensing units as disclosed herein. In some embodiments, the method further comprises determining fetal ballistocardiography data from abdominal acoustic wave data obtained through inclinometer sensing units. In some embodiments, the method is for determining fetal phonocardiography data from abdominal acoustic wave data obtained through MEMS accelerometer sensing units. In some embodiments, the method is for determining fetal movement data from abdominal acoustic wave data obtained through MEMS accelerometer sensing units. In some embodiments, the method for determining fetal heartrate data from abdominal pressure wave data obtained through diaphragm or ferroelectric nanogenerator sensing units. In some embodiments, the method is for determining fetal movement data from abdominal pressure wave data obtained through diaphragm or ferroelectric nanogenerator sensing units. In some embodiments, the method is for use of audio source separation for separating fetal movement from abdominal acoustic signal. In some embodiments, the method is for use of audio source separation for separating fetal phonocardiogram from abdominal acoustic signal. In some embodiments, the method is for assessing fetal health based on various input conditions.

Provided herein is a wearable system for intrapartum monitoring of fetal health comprised of at least some of the following: a band configured to be worn on a torso of an expecting mother; and a maternal pulse oximeter engaged with the band for collecting maternal heartbeat and capillary oxygen saturation information. The wearable system can also include one or more sensors comprising one of: inclinometers for collecting low frequency abdominal acoustic wave information; one or more accelerometers for collecting mid frequency abdominal acoustic wave information; one or more acoustic sensors for collecting fetal health audio information; and a computer control system having memory and a processor configured for comparing data from the material pulse oximeter and the one or more sensors for determining a health characteristic of the mother or patient.

Although the illustrative embodiments of the present invention have been described herein with reference to the accompanying drawings, it is to be understood that the invention is not limited to those precise embodiments and that various other changes and modifications may be effected therein by one skilled in the art without departing from the Scope or spirit of the invention As to the above, they are merely specific embodiments of the present invention; however, the scope of protection of the present invention is not limited thereto, and within the disclosed technical scope of the present invention, any modifications or substitutions that a person skilled in the art could readily conceive of should fall within the scope of protection of the present invention. Thus, the scope of protection of the present invention shall be determined by the scope of protection of the appended claims.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

These and other changes can be made to the disclosure in light of the Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

What is claimed is:

1. A fetal monitoring patch for determining a health condition of a fetus based on biosignals of an expecting mother and the fetus, the fetal monitoring patch comprising:
   a first acoustic sensor configured to provide mechano-acoustically sensed phonocardiogram (aPCG) data from an anterior side location on a maternal torso;
   an optical sensor configured to provide optically sensed maternal photoplethysmogram (mPPG) data from an anterior centralized location on the maternal torso relative to the anterior side location;
   a breathable substrate configured to provide skin contact of the first acoustic sensor via a first acoustic impedance coupler and skin contact of the optical sensor to the maternal torso for continuous non-invasive non-clinical monitoring; and
   a microcontroller mechanically coupled with the breathable substrate, wherein the microcontroller is configured for:
      continuously monitoring fetal movement (fM) using the first acoustic sensor while operating in a first mode, wherein the first mode is a low-power vigilant monitoring state; and
      upon detecting reduced fM activity, transitioning to a second mode comprising:
         decomposing the mechano-acoustically sensed aPCG data using the optically sensed mPPG data to extract mechano-acoustically sensed fetal phonocardiogram (fPCG) data;
         determining fetal heart rate variability (fHRV) data from the mechano-acoustically sensed fPCG data; and
         providing an alert to the expecting mother based on the fHRV data, wherein the alert is indicative of a medical emergency.

2. The fetal monitoring patch of claim 1, wherein the microcontroller is further configured to calculate fetal movement (fM) data from the mechano-acoustically sensed aPCG data.

3. The fetal monitoring patch of claim 1, wherein:
   the optical sensor is further configured to sense maternal peripheral capillary oxygen saturation (mSpO2) data; and
   transitioning to the second mode is further based upon detecting reduced mSpO2 data.

4. The fetal monitoring patch of claim 1, wherein the microcontroller is further configured to calculate a maternal activity level from the optical sensor.

5. The fetal monitoring patch of claim 1, further comprising one or more of: a MEMS inclinometer, an inertia sensor, and a gyroscope.

6. The fetal monitoring patch of claim 1, further comprising a patch configured to removably attach to the maternal torso.

7. The fetal monitoring patch of claim 1, further comprising an inclinometer sensor that detects a sub-audible abdominal acoustic wave.

8. The fetal monitoring patch of claim 1, wherein a first portion of the fetal monitoring patch is disposable, and a second portion of the fetal monitoring patch is re-usable.

9. The fetal monitoring patch of claim 1 further comprising:
- a second acoustic sensor configured to provide mechano-acoustically sensed aPCG data from an opposite anterior side location on the maternal torso; and
- a noise attenuator configured to: at least partially constructively or destructively combine a first physiological signal component of a first signal output by the first acoustic sensor and a second physiological signal component of a second signal output by a second acoustic sensor.

10. The fetal monitoring patch of claim 9, wherein the anterior centralized location is lower on the maternal torso than both the anterior side location and the opposite anterior side location.

11. The fetal monitoring patch of claim 10, wherein the anterior centralized location is closer to the anterior side location than to the opposite anterior side location.

12. The fetal monitoring patch of claim 1, wherein determining fHRV data from the mechano-acoustically sensed fPCG data comprises using empirical mode decomposition (EMD).

13. The fetal monitoring patch of claim 1, wherein the anterior centralized location is lower on the maternal torso than the anterior side location on the maternal torso.

14. The fetal monitor patch of claim 1, wherein the fetal monitoring patch is configured as a singular unit in a form of a wearable pressure adhesive patch.

15. A method of determining a health condition of a fetus based on biosignals of an expecting mother and the fetus, the method comprising:
- providing a fetal monitoring patch, comprising:
  - a first acoustic sensor configured to provide mechano-acoustically sensed phonocardiogram (aPCG) data from an anterior side location on a maternal torso;
  - an optical sensor configured to provide optically sensed maternal photoplethysmogram (mPPG) data from a second an anterior centralized location on the maternal torso relative to the anterior side location;
  - a breathable substrate configured to provide skin contact of the first acoustic sensor via a first acoustic impedance coupler and skin contact of the optical sensor to the maternal torso for continuous non-invasive non-clinical monitoring; and
  - a microcontroller mechanically coupled with the breathable substrate, wherein the microcontroller is configured for:
    - continuously monitoring fetal movement (fM) using the first acoustic sensor while operating in a first mode, wherein the first mode is a low-power vigilant monitoring state; and
    - upon detecting reduced fM activity, transitioning to a second mode comprising:
      - decomposing the mechano-acoustically sensed aPCG data using the optically sensed mPPG data to extract mechano-acoustically sensed fetal phonocardiogram (fPCG) data;
      - determining fetal heart rate variability (fHRV) data from the mechano-acoustically sensed fPCG data; and
      - providing an alert to the expecting mother based on the fHRV data, wherein the alert is indicative of a medical emergency.

16. The method of claim 15, further comprising outputting at least one of a normal state, caution state, and emergency state based on the mechano-acoustically sensed fPCG data.

17. The method of claim 15, further comprising calculating fetal movement (fM) data from the mechano-acoustically sensed aPCG data.

18. A non-transitory computer-readable storage medium, the non-transitory computer-readable storage medium storing instructions to be implemented on a fetal monitoring patch comprising:
- a first acoustic sensor configured to provide mechano-acoustically sensed phonocardiogram (aPCG) data from an anterior side location on a maternal torso;
- an optical sensor configured to provide optically sensed maternal photoplethysmogram (mPPG) data from an anterior centralized location on the maternal torso relative to the anterior side location;
- a breathable substrate configured to provide skin contact of the first acoustic sensor via a first acoustic impedance coupler and skin contact of the optical sensor to the maternal torso for continuous non-invasive non-clinical monitoring; and
- at least one processor mechanically coupled with the breathable substrate; the instructions when executed by the at least one processor cause the fetal monitoring patch to perform a method of determining a health condition of a fetus based on biosignals of an expecting mother and the fetus, the method comprising:
  - continuously monitoring fetal movement (fM) using the acoustic sensor while operating in a first mode, wherein the first mode is a low-power vigilant monitoring state; and
  - upon detecting reduced fM activity, transitioning to a second mode comprising:
    - decomposing the mechano-acoustically sensed aPCG data using the optically sensed mPPG data to extract mechano-acoustically sensed fetal phonocardiogram (fPCG) data;
    - determining fetal heart rate variability (fHRV) data from the mechano-acoustically sensed fPCG data; and
    - providing an alert to the expecting mother based on the fHRV data, wherein the alert is indicative of a medical emergency.

* * * * *